United States Patent
Roesch et al.

(10) Patent No.: US 7,770,432 B2
(45) Date of Patent: Aug. 10, 2010

(54) SENSOR ELEMENT FOR PARTICLE SENSORS AND METHOD FOR OPERATING SAME

(75) Inventors: Sabine Roesch, Ditzingen (DE); Thorsten Ochs, Schwieberdingen (DE); Bernhard Kamp, Ludwigsburg (DE); Henrik Schittenhelm, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 356 days.

(21) Appl. No.: 11/795,704

(22) PCT Filed: Jan. 13, 2006

(86) PCT No.: PCT/EP2006/050196

§ 371 (c)(1),
(2), (4) Date: Mar. 11, 2008

(87) PCT Pub. No.: WO2006/077197

PCT Pub. Date: Jul. 27, 2006

(65) Prior Publication Data

US 2008/0264146 A1    Oct. 30, 2008

(30) Foreign Application Priority Data

Jan. 21, 2005    (DE) ...................... 10 2005 003 118

(51) Int. Cl.
*G01N 31/00*    (2006.01)
(52) U.S. Cl. ................................. 73/23.33; 73/304 C
(58) Field of Classification Search ............... 73/23.33, 73/304 C, 304 R
See application file for complete search history.

(56) References Cited

U.S. PATENT DOCUMENTS

| 5,457,396 | A | 10/1995 | Mori et al. |
| 6,634,210 | B1 | 10/2003 | Bosch et al. |
| 2001/0035044 | A1 | 11/2001 | Larsson et al. |
| 2001/0051108 | A1 | 12/2001 | Schonauer |
| 2003/0196499 | A1 | 10/2003 | Bosch et al. |

*Primary Examiner*—Hezron Williams
*Assistant Examiner*—Rodney T Frank
(74) *Attorney, Agent, or Firm*—Kenyon & Kenyon LLP

(57) ABSTRACT

A sensor element for gas sensors for determining the concentration of particles in gas mixtures, especially soot sensors, having at least one measuring device exposed to the gas to be determined, at least one heating element integrated into the sensor element and at least one temperature measurement element integrated into the sensor element, the heating element being situated within the sensor element spatially between the measuring device and the temperature measurement element.

14 Claims, 1 Drawing Sheet

SENSOR ELEMENT FOR PARTICLE SENSORS AND METHOD FOR OPERATING SAME

FIELD OF THE INVENTION

The present invention relates to a sensor element and a method for determining the concentration of particles in gas mixtures, as well as their use.

BACKGROUND INFORMATION

Along with the tendency towards ever more binding environmental laws, exhaust gas aftertreatment systems, which make possible the filtration or elimination of soot particles existing in combustion exhaust gases, are increasingly attaining importance. In order to check or to monitor the reliability of such exhaust gas aftertreatment systems, sensors are required by the use of which, even in the long run, an accurate ascertainment can be made of the instantaneous particle concentration present in the combustion exhaust gas. In addition, by the use of such sensors, it should become possible to make a prognosis of the degree of saturation of a Diesel particulate filter provided in an exhaust gas system, in order to attain a high degree of system safety and thereby be able to use more cost-effective filter materials.

A sensor is described in U.S. Pat. No. 6,634,210 for detecting substances in a fluid flow, which is developed on the basis of a ceramic multi-layer substrate. It includes two measuring electrodes, at a distance from each other, which are exposed to the combustion exhaust gas that is to be tested. If soot deposits between the two measuring electrodes, this produces a current flow between the measuring electrodes in response to the application of a voltage to the measuring electrodes. A heating element, designed in the form of layers, makes it possible to free the electrodes and their surroundings from deposited soot particles by way of a thermal process. The sensor also includes a temperature measurement element by which the temperature of the sensor can be detected. The temperature measurement element is located within the laminar structure of the sensor, between the heating element and the measuring electrodes. What is disadvantageous in this construction of the sensor is that the temperature ascertained via the temperature measurement element does not correspond to that temperature which prevails in the region of the measuring electrodes.

It is an object of the present invention to provide a sensor element for sensors, and a method for determining the concentration of particles in gas mixtures which permits an accurate temperature regulation and yet can be carried out in a cost-effective manner.

SUMMARY OF THE INVENTION

The sensor element and the method according to the present invention have the advantage that the object, on which the present invention is based, is attained in an advantageous manner. This is based particularly on the simple construction of the sensor element and on the fact that the heating element is situated within the sensor element, spatially between a measuring device and a temperature measurement element of the sensor element. In this context, a symmetrical arrangement is particularly provided of the temperature measurement element and the measuring electrodes, with respect to the position of the heating element within the sensor element and with respect to the large surfaces of the sensor element.

Thus, it is of advantage if the measuring electrodes are preferably embodied as interdigital electrodes that are interleaved with one another, since in this way the electrical resistance and the electrical conductivity of large surface areas can be determined under specified circumstances, and the sensitivity and quality of the measurement signals are thus clearly improved.

In one particularly advantageous specific embodiment of the present invention, an evaluation device is provided which ascertains a change in the current flow present between the measuring electrodes, and which outputs this as a measurement for the particulate concentration.

It is also an advantage if the measuring electrodes of the sensor element are situated in the same layer plane as the heating element and/or the temperature measurement element, since the construction of the sensor element is clearly able to be simplified thereby.

The sensor element and the method for operating it is suitable in an advantageous manner for monitoring the operating method of a Diesel engine and for monitoring the reliability or the degree of saturation of a particulate filter.

DETAILED DESCRIPTION

Figures 1, 2:
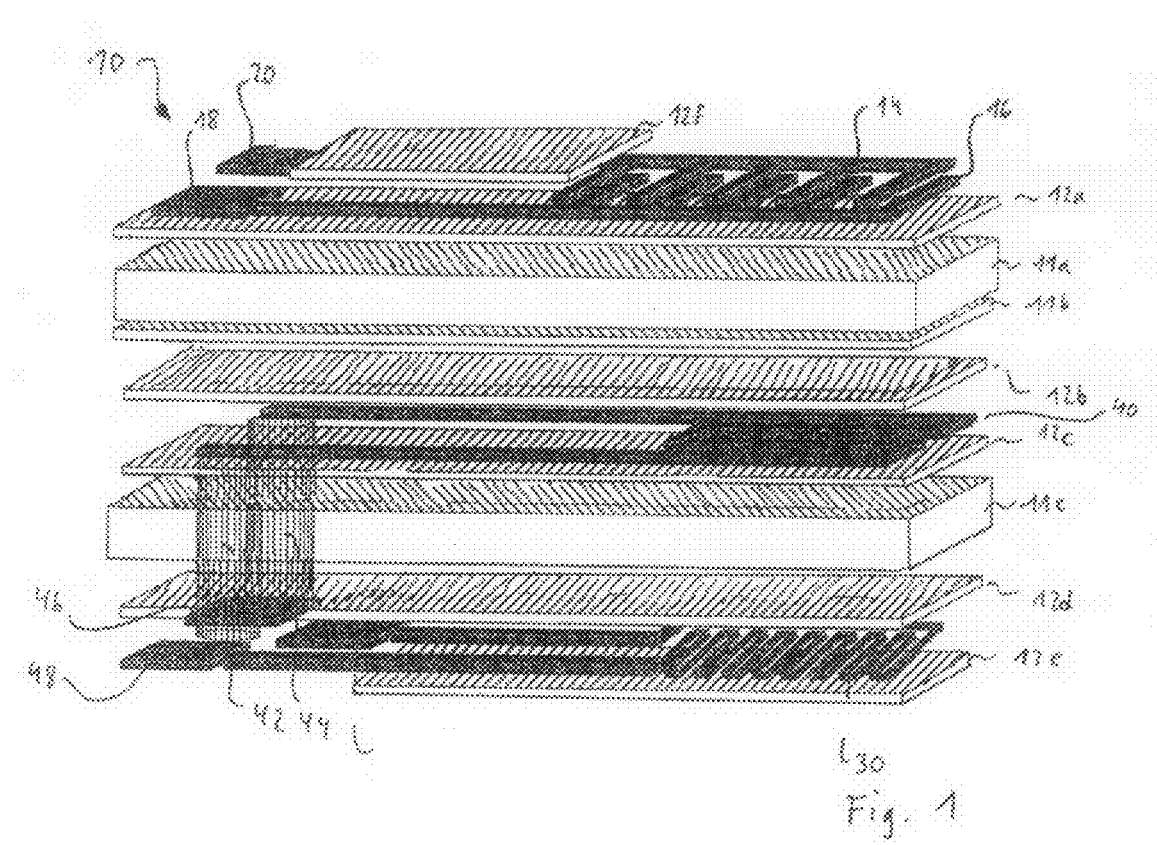
FIG. 1 shows a sensor element, in this instance, according to a first exemplary embodiment, in an exploded representation.
FIG. 2 shows a sensor element, in this instance, according to a second exemplary embodiment, in a top view.

FIG. 1 shows a schematic of the structure of a specific embodiment according to the present invention. A ceramic sensor element is designated by 10, and it is used for determining a particulate concentration, such as the soot concentration in a gas mixture surrounding the sensor element. Sensor element 10 includes, for example, a plurality of oxygen ion-conducting solid electrolyte layers 11$a$, 11$b$ and 11$c$. In this context, solid electrolyte layers 11$a$ and 11$d$ are designed as ceramic foils, and form a planar ceramic body. They are made of a solid-electrolyte material that conducts oxygen ions, such as $ZrO_2$ stabilized or partially stabilized using $Y_2O_3$.

In contrast, solid electrolyte layer 11$b$ is produced by screen-printing a pasty ceramic material, that is, for instance, generated on solid electrolyte layer 11$a$. The same solid electrolyte material is preferably used as a ceramic component of the pasty material as the one which also makes up solid electrolyte layers 11$a$, 11$c$.

Furthermore, the sensor element has a plurality of electrically insulating ceramic layers 12$a$, 12$b$, 12$c$, 12$d$, 12$e$ and 12$f$. Layers 12$a$-12$f$ are also generated, for instance, on solid electrolyte layers 11$a$, 11$b$, 11$c$, in this context, using screen printing of a pasty ceramic material. Barium-containing aluminum oxide is used, for example, as the ceramic component of the pasty material, in this instance, since to a great extent it has a constantly high electrical resistance, even in response to stresses caused by temperature changes over a long period of time. Alternatively, one may also use cerium dioxide or the addition of other earth alkali oxides.

The integrated form of the planar ceramic body of sensor element 10 is produced in a known manner, by laminating together the ceramic foils printed over with solid electrolyte layer 11$b$ and functional layers, and by subsequently sintering the laminated structure.

Moreover, sensor element 10 has a ceramic heating element 40, which is developed as an electrical resistance circuit board conductor and is used for heating up sensor element 10, particularly to the temperature of the gas mixture to be determined and for burning off soot particles deposited on the large surfaces of sensor element 10. The resistance circuit board conductor is preferably developed of a cermet material; preferably as a mixture of platinum or a platinum metal having ceramic proportions, such as aluminum oxide. The resistance circuit board conductor is also preferably developed in a meandering form, and at both ends it has plated through-holes 42, 44, as well as electrical connections 46, 48. By applying an appropriate heating voltage to connections 46, 48 of the resistance circuit board conductor, the heating performance of heating element 40 can be appropriately regulated.

On one large surface of sensor element 10, for example, two measuring electrodes 14, 16 are applied, which are preferably developed as interdigital electrodes that are interleaved with each other. The use of interdigital electrodes as measuring electrodes 14, 16 advantageously makes possible an especially accurate determination of the electrical resistance and the electrical conductivity of the surface material located between measuring electrodes 14, 16. Contact surfaces 18, 20 are provided for contacting measuring electrodes 14, 16, in the area of the end of the sensor element that faces away from the gas mixture. In this context, the supply lead areas of electrodes 14, 16 are preferably shielded by an additional, electrically insulating ceramic layer 12f from the influences of a gas mixture surrounding sensor element 10.

On the large surface of sensor element 10 that is furnished with measuring electrodes 14, 16, a porous layer, that is not shown for reasons of clarity, can be provided in addition, which shields measuring electrodes 14, 16, in their area of being interleaved with one another, from a direct contact with the gas mixture that is to be determined. The layer thickness of the porous layer, in this instance, is preferably greater than the layer thickness of measuring electrodes 14, 16. The porous layer is preferably developed to be open-pored, the pore size being selected so that the particles to be determined in the gas mixture are able to diffuse into the pores of the porous layer. The pore size of the porous layer, in this instance, is preferably in a range of 2 to 10 µm. The porous layer is developed of a ceramic material which preferably is similar to the material of layer 12a, or is equivalent to it, and can be produced using screen printing. The porosity of the porous layer can be adjusted correspondingly by adding pore-forming materials to the screen printing paste.

During the operation of sensor element 10, a voltage is applied to measuring electrodes 14, 16. Since measuring electrodes 14, 16 are situated on the surface of electrically insulating layer 12a, there is first of all essentially no current flow between measuring electrodes 14, 16.

If a gas mixture flowing around sensor element 10 contains soot, in particular, it will deposit on the surface of sensor element 10. Because of the open-pored structure of the porous layer, the particles diffuse all the way through the porous layer up to the immediate vicinity of measuring electrodes 14, 16.

If there is sufficient saturation of the surface of sensor element 10 or the porous layer with soot, since soot has a certain electrical conductivity, an increasing current flow will ensue between measuring electrodes 14, 16, which correlates with the extent of the saturation.

Now, if preferably a constant direct voltage or alternating voltage is applied to measuring electrodes 24, 26, and the current flow occurring between measuring electrodes 24, 26 is determined, one can draw conclusions, from the integral over time of the current flow, concerning the deposited particle mass and the instantaneous particle mass flow, in particular the soot mass flow, and concerning the particle concentration in the gas mixture. Using this measuring method, the concentration is recorded of all those particles in a gas mixture which positively or negatively influence the electrical conductivity of the ceramic material located between measuring electrodes 24, 26.

A further possibility is ascertaining the increase in the current flow over time, and to draw a conclusion, from the quotient of current flow increase and time, or rather, from the differential quotient of current flow with respect to time, as to the deposited particle mass and as to the instantaneous particle mass flow, particularly the soot mass flow, and as to the particle concentration in the gas mixture. A calculation of the particle concentration can be made based on the measured values, to the extent that the speed of flow of the gas mixture is known. This and the volume flow of the gas mixture can be determined, for instance, using a suitable additional sensor.

In addition, sensor element 10 includes a temperature measurement element 30, which is preferably developed in the form of an electrical resistance circuit board conductor. The resistance circuit board conductor is developed, for instance, of a similar or the same material as that of the resistance circuit board conductor of heating element 40. The resistance circuit board conductor of temperature measurement element 30 is preferably developed in meandering form, one of the connections of the resistance circuit board conductor being preferably connected to ground via connection 48. In addition, temperature measurement element 30 has a further electrical connection 32. By applying an appropriate voltage to connections 32, 48 of the resistance circuit board conductor, and by determining its electrical resistance, one can draw a conclusion concerning the temperature of the sensor element. Alternatively, one can make a temperature determination using thermocouples. A further alternative or additional possibility of measuring temperature is to determine the per se temperature-dependent conductivity of the ceramic element situated between the resistance circuit board conductor of temperature measurement element 32 and measuring electrodes 24, 26, and to conclude, from its magnitude, the temperature of the sensor element.

The electrical resistance of the material located between measuring electrodes 14, 16, determined using measuring electrodes 14, 16, is subject to a great temperature dependence. This being the case, as exact as possible a determination of the sensor temperature occurring in the area of measuring electrodes 14, 16 is an important assumption for obtaining usable measuring results. Since, however, for spatial reasons, a temperature determination in the immediate vicinity of measuring electrodes 14, 16 can often not be implemented, measuring electrodes 14, 16, heating element 40 and temperature measurement element 30 are spatially positioned within sensor element 10 in such a way that heating element 40 is situated in a layer plane which is located between the layer plane that includes measuring electrodes 14, 16 and the layer plane including temperature measurement element 30. Especially if measuring electrodes 14, 16 and temperature measurement element 30 are essentially at the same distance from heating element 40, in this instance, it is true that measuring electrodes 14, 16 and temperature measurement element 30 are situated in different regions of sensor element 10, but it may be supposed, because of an essentially comparable distance of measuring electrodes 14, 16 and temperature element 30 from heating element 40, that a comparable temperature prevails at measuring electrodes 14, 16 as that which is recorded by temperature measurement element 30. By making a temperature determination using temperature measurement element 30, one can effectively draw a conclusion on what the temperature is of measuring electrodes 14, 16 because of a spatial arrangement of heating element 40 between measuring electrodes 14, 16 and temperature measurement element 30, particularly if there is a symmetrical or equidistant arrangement of heating element 40 with respect to measuring electrodes 14, 16 and temperature measurement element 30. This makes possible an effective consideration of the current temperature of the sensor element in the determination of the electrical resistance over measuring electrodes 14, 16.

FIG. 2 shows a sensor element according to a second exemplary embodiment. In this context, identical reference numerals designate the same components as in FIG. 1.

The sensor element according to a second exemplary embodiment, shown in a top view, represents an additional possibility as to how the positioning of heating element 40 and measuring electrodes 14, 16 on the one hand, and temperature measurement element 30 on the other hand can be implemented. Both electrodes 14, 16 and also heating element 40 and temperature measurement element 30 have been applied onto electrically insulating layer 12a. Heating element 40, in this instance, is situated spatially in the same layer plane of the sensor element between the resistance circuit board conductor of temperature measurement element 30 and measuring electrodes 14, 16. This preferably takes place in such a way that at least the heating range of heating element 40 is essentially at the same distance from measuring electrodes 14, 16 as from temperature measurement element 30. In this way, a symmetrical and/or equidistant arrangement of heating element 40 with respect to measuring electrodes 14, 16 and temperature measurement element 30 are achieved; in addition, the layer construction can be reduced to few ceramic layers. However, the resistance circuit board conductors of heating element and temperature measurement element 30, 40 are preferably covered by additional ceramic layer 12f against corrosive influences of the gas mixture that is to be determined.

The present invention is not restricted to the specific embodiments of a sensor element shown in FIGS. 1 and 2, but rather numerous modifications of this sensor element can be undertaken. Thus, it is possible, for example, to provide additional ceramic layers in the sensor element or to simplify the multi-layer construction of the sensor element with reference to the application, as well as to provide additional measuring electrodes. The use of a plurality of heating elements and temperature measurement element is also a possibility.

The use of the sensor element described is not restricted to the determination of soot particles in exhaust gases of internal combustion engines, but it can be used quite generally for determining the concentration of particles which change the electrical conductivity of a ceramic substrate in response to intercalation, for instance, in chemical preparation processes or in exhaust air aftertreatment systems.

What is claimed is:

1. A sensor element for a gas sensor for determining a concentration of particles in a gas mixture, comprising:
   at least one measuring device exposed to a gas to be determined;
   at least one temperature measurement element integrated into the sensor element; and
   at least one heating element integrated into the sensor element, the heating element being situated within the sensor element spatially between the measuring device and the temperature measurement element.

2. The sensor element according to claim 1, wherein the sensor element is for a soot sensor.

3. The sensor element according to claim 1, wherein the measuring device includes a first and a second measuring electrode, using which an electrical resistance is able to be determined.

4. The sensor element according to claim 3, wherein each of the first and the second measuring electrode is an interdigital electrode.

5. The sensor element according to claim 3, wherein the first and the second measuring electrode are situated on an electrically insulating substrate, the electrically insulating substrate including at least one of aluminum oxide and alkaline earth oxide.

6. The sensor element according to claim 3, further comprising an evaluating device for ascertaining a change in at least one of a current flow and a resistance present between the measuring electrodes, and outputting this as a measure for a particulate concentration.

7. The sensor element according to claim 3, wherein each of the first and the second measuring electrode is situated in the same layer plane as at least one of the heating element and the temperature measurement element.

8. A sensor element for a gas sensor for determining a concentration of particles in a gas mixture, comprising:
   at least one measuring device exposed to a gas to be determined;
   at least one heating element integrated into the sensor element; and
   at least one temperature measurement element integrated into the sensor element,
   wherein the measuring device and the temperature measurement element are substantially equidistant from at least one of (a) the heating element and (b) large surfaces of the sensor element.

9. The sensor element according to claim 8, wherein the sensor element is for a soot sensor.

10. A method for determining a concentration of particles in a gas mixture using a sensor element, the method comprising:
    applying a voltage to at least two measuring electrodes;
    determining a current flow ensuing between the measuring electrodes; and
    outputting the current flow as a measure for a particulate concentration.

11. The method according to claim 10, wherein the method is for determining a concentration of soot in exhaust gases of an internal combustion engine.

12. The method according to claim 10, further comprising initiating a regeneration of the sensor element as soon as a current flow ensuing between the measuring electrodes at least one of (a) exceeds a predetermined value and (b) assumes a constant value for a predetermined time period.

13. The method according to claim 10, wherein the method is used for monitoring an operating method of a Diesel engine.

14. The method according to claim 10, wherein the method is used for monitoring at least one of a reliability and a degree of saturation of a particulate filter.

* * * * *